United States Patent [19]

Pearlman et al.

[11] Patent Number: 5,347,992
[45] Date of Patent: Sep. 20, 1994

[54] SINGLE AXIS THREE WAY SELECTOR VALVE FOR ENDOSCOPES

[75] Inventors: Marshall B. Pearlman; Eric M. Jones, both of Los Angeles, Calif.

[73] Assignee: Karl Storz Endoscopy America, Inc., Culver City, Calif.

[21] Appl. No.: 8,788

[22] Filed: Jan. 22, 1993

[51] Int. Cl.5 .............................. A61B 1/00
[52] U.S. Cl. .......................... 128/4; 604/33; 137/630.16
[58] Field of Search ............... 128/4, 5; 604/30, 33, 604/35, 246, 249, 118, 119, 121, 902; 251/321, 325; 137/628, 630.16, 627.5

[56] References Cited

U.S. PATENT DOCUMENTS

| | | | |
|---|---|---|---|
| 3,608,946 | 9/1971 | Erickson | 604/902 X |
| 3,678,959 | 7/1972 | Liposky | 604/33 X |
| 4,261,343 | 4/1981 | Ouchi et al. | 128/4 |
| 4,680,026 | 7/1987 | Weightman et al. | 604/902 X |
| 4,881,523 | 11/1989 | Heckele | 128/4 |
| 5,027,791 | 7/1991 | Takahashi | 128/4 |
| 5,034,000 | 7/1991 | Freitas et al. | 604/30 |

FOREIGN PATENT DOCUMENTS 0199876  11/1986  European Pat. Off. ......... 128/4

Primary Examiner—Richard J. Apley
Assistant Examiner—Karen A. Jalbert
Attorney, Agent, or Firm—Donald D. Mon

[57] ABSTRACT

A single axis three way valve for endoscopes. The valve has a repose, closed setting and two active settings. In one active setting, a common port to the endoscope is connected to suction, and in the other active setting it is connected to a source of irrigation liquids. The valve has two spools, one of which is connected to a finger pad for actuation, and which is spring-loaded to a closed position. The other spool is spaced from the first, and also is spring-loaded closed . The first valve is opened by initial movement. Further movement closes its port and abuts the other spool to open its respective port.

9 Claims, 2 Drawing Sheets

SINGLE AXIS THREE WAY SELECTOR VALVE FOR ENDOSCOPES

FIELD OF THE INVENTION

This invention relates to a three way selector valve which is especially advantageous for use in endoscopic procedures.

BACKGROUND OF THE INVENTION

During endoscopic procedures, the surgeon must frequently irrigate and then suction a region in which he is operating. He is customarily provided with a handpiece that includes two trumpet-type valves, one for the liquid and the other for suction. His task in addition to manipulation of the various optical and surgical appliances associated with an endoscope is to irrigate regions of interest, and to suction out liquids and debris. Anything which can simplify this assortment of tasks is a welcome improvement. Convenience of grasp is a further convenience. If an appliance can only be gripped in one orientation, it is likely that in other alignments it will be inconvenient to manipulate.

Known two-valve arrangements are an example of devices to which improvements would be welcomed. In these devices, two valves are arranged side-by-side, their axes parallel, with a separate valve for each. The surgeon must either switch one finger from one button to the other, remembering which is which, or keep a finger on each, again remembering which is which. There is a single orientation in which the valve can be held much like a musical trumpet. Thus there is a lack of versatility, and a potentially irksome need for excessive memory and manipulation, often in an inconvenient orientation.

It is an object of this invention to provide a three way selector valve which requires only a single actuator button to set the device for no flow into or out of a common port, or flow into or out of it from or to a selected one of two source ports. In one conventional application, the common port will be connected to a conduit in the endoscope for bi-directional flow, one of the source ports will be connected to a source of saline solution for irrigation, and the other will be connected to a suction pump for removal of fluids and debris.

Because of this arrangement, short circuiting between the source ports is impossible, in its active settings and if desired audible, tactile, or visual means can indicate the direction of flow.

The valve body is configured to permit it to be grasped so that an index finger can press the button, rather as a pistol grip in either hand- right or left handed, and also so it can be held in such a way that the thumb can press it down, rather as a hypodermic syringe. This versatility of grip orientation is a significant convenience to the surgeon.

BRIEF DESCRIPTION OF THE INVENTION

A valve body includes a common channel for communicating with an endoscope, and a valve bore which has a central axis. A common port interconnects the common channel and the valve bore.

A first source port and a second source port open into the valve bore on axially opposite sides of the common port.

A first valve spool is slidingly and sealingly fitted in the valve bore. It carries a pair of axially spaced apart peripheral seals whose spacing apart enables them to straddle and thereby isolate the first source port from the remainder of the bore when they do straddle the first source port in the rest position of this spool.

First spring bias means biases the first valve spool toward said rest position relative to the location of the common port with all paths closed. A stop shoulder in the valve bore and a stop shoulder on the first valve spool define this rest position. In this position the first source port is closed to flow. When axially shifted against the first spring bias means, the first source port will be opened to flow.

A second valve spool is also slidingly fitted in the valve bore. It has peripheral seals whose spacing apart enables them to straddle and thereby isolate the second source port from the remainder of the bore when they do straddle the second source port in its respective rest position.

Second spring bias means biases the second valve spool in the axial direction away from the common port. A stop shoulder in the valve bore and a stop shoulder on the second valve spool define this rest position. An inlet relief is formed in the second valve spool. An axially extending flow passage extends in the second valve spool from the relief to the end closest to the common port, whereby when the second valve spool is axially shifted against the second spring bias means so the relief is aligned with the second source port, the second source port is communicated with the common port.

When the second valve spool is shifted so the relief has moved past the second source port, the contact means will have shifted the first valve spool to open the first valve port.

Contact means on each of the spools face one another, and when in the rest positions of the spools, the contact means are spaced apart by the axial length required to move the second valve spool needed to align the relief with the second source port.

Two pairs of axially spaced apart seals are disposed on the second spool so as to bound the inlet relief, and two closure regions, one on each side of the relief. When the relief is on either side of the second source port, the second source port is closed.

Selection of which of the source ports is connected to the common port therefore requires only the shifting of the second spool between the two last-named positions. To close the valve to all flow, the spool is released and the two bias springs move the spools to their closed rest positions.

According to a preferred but optional feature of this invention, the second valve spool is provided with a projecting actuator button, and the body is scalloped to enable it to be grasped in a plurality of orientations relative to hand.

This invention will be fully understood from the following detailed description and the accompanying drawings, in which:

DETAILED DESCRIPTION OF THE INVENTION

Figure 1:
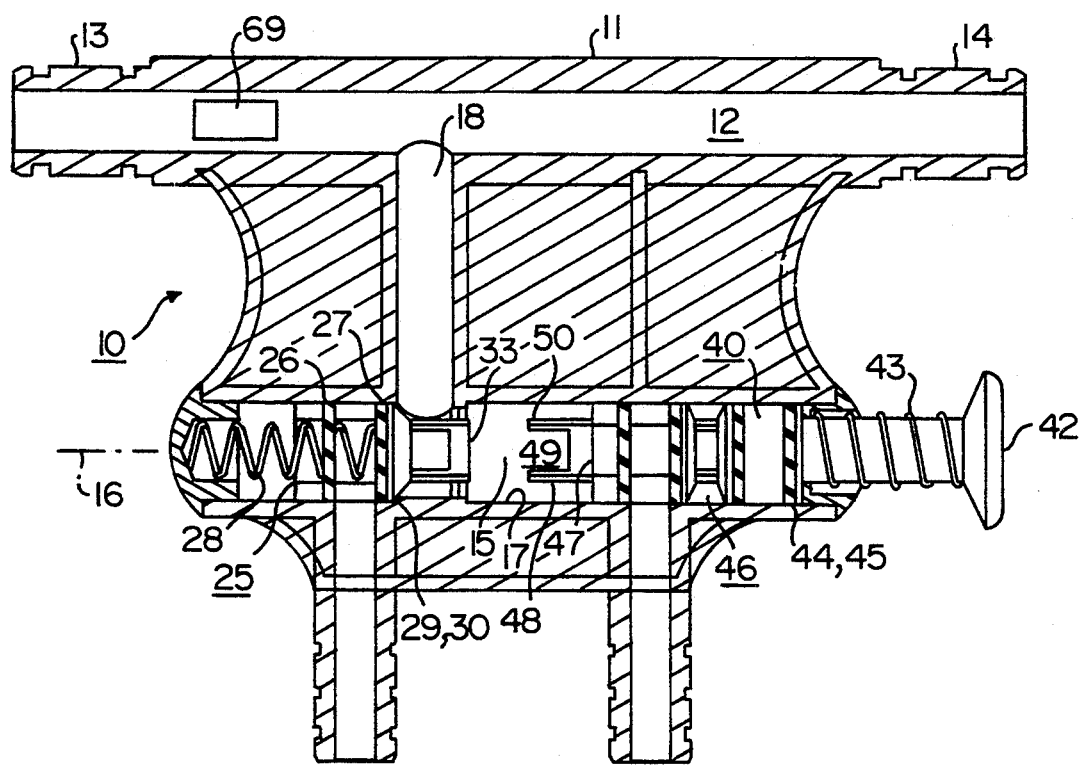
FIG. 1 is a cross-section taken at line 1—1 in FIG. 2 showing the valve in its closed, rest, condition.
Figure 2:
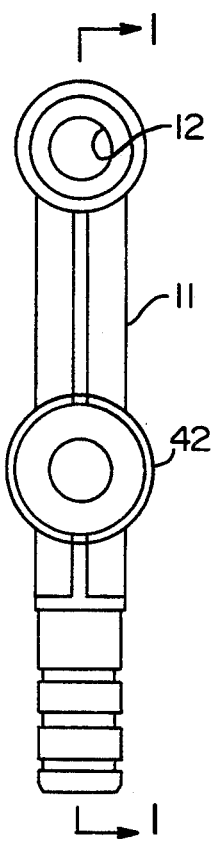
FIG. 2 is a side view of FIG. 1.

A valve 10 according to this invention has a body 11, usually generally flat. The body, and all other parts except for the springs and seals may be made of rigid molded organic plastic material such as Delrin.

A common channel 12 extends from edge to edge of the body. Necks 13,14 can selectively receive plugs or connections (not shown) to endoscopic instruments.

A valve bore 15 has an axis 16 and a circular cylindrical interior wall 17. A common port 18 extends between wall 17 and common channel 12.

A first source port 20 extends through the body and into bore 15. A second source port 21 enters through the body and into bore 15. Common port 18 enters through the body and into bore 15. Ports 20 and 21 are on opposite sides of common port 18.

A first valve spool 25 is slidingly fitted in valve bore 15. It carries a pair of spaced apart peripheral seals 26,27 which can span the axial width of first source port 20. A first bias spring 28 biases spool 25 to the right in the Figs. A stop shoulder 29 on the spool and a stop shoulder 30 in the bore limit the movement of spool 25 toward the common port. In FIG. 1, the rest position of spool 25 is shown. There is then no communication between bore 15 and port 20.

Spool 25 has contact means 31, whose lateral dimensions are smaller than those of the valve bore. Also, to facilitate flow, these contact means are tubular, with a fenestration 32, so that the contact means do not constitute a limitation on flow when the first valve spool permits it. Contact surface 33 is the end of this tubular construction.

A second valve spool 40 has an extension 41 to a finger pad 42. A bias spring 43 between the valve body and the spool biases spool 40 to the right in FIGS. 1 and 3. Stops 44 and 45 on the spool arm in the body limit the movement of the second valve spool as shown in FIG. 1. This is the rest position of second valve spool 40.

Valve spool 40 has a peripheral inlet relief 46 which opens into a flow passage 47 in the valve spool. Flow passage 47 extends from the inlet relief to the end of the second valve spool closest to common port 18.

Passage 47 opens into contact means 48, which has a notch 49 for fluid flow, and a contact surface 50 which is aligned with contact surface 33 on the first valve spool so they can react with one another for cooperative axial movement.

There is a pair of seals 55,56 on one side of relief 46, and another pair of seals 57,58 on the other side.

Adjacent seals are axially spaced from each other far enough to span the second source port, and the centermost seals are spaced far enough apart to span source port 21, also.

The operation of this valve is straight forward. With the source ports connected to their sources and the common channel connected to the endoscope, the surgeon finds the valve in the rest condition shown in FIG. 1. The actuator button is available but not depressed. Accordingly both spools are biased to their illustrated position. Both source ports are closed. The seals on the first spool span the first port. The left hand pair of seals on the second valve spool span the second source port.

When the second spool is first pressed, it is moved so that seals 56 and 57 span the second source port, and inlet relief 46 communicates with second source port 21. First source port 20 is still closed, because the contact means will have just met, but have not moved the first spool.

Accordingly, second source port 21 and common port 18 are communicated through flow passage 47. This is one of the two active settings of this valve.

Figure 3:
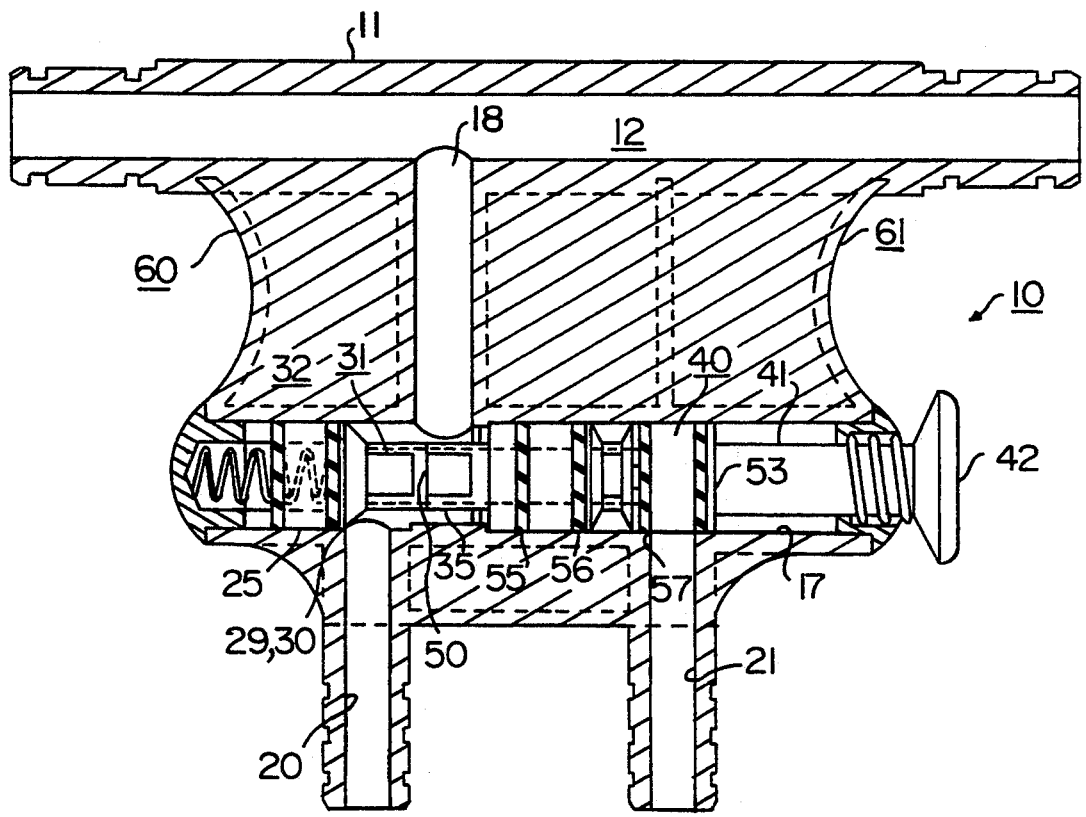
FIG. 3 is a modified cross-section similar to FIG. 1 showing the valve in one of its actuated conditions.

The next incremental movement of the second valve spool also moves the first valve spool, because the contact means bear against one another. Now seals 57 and 58 span the second source port to close it, but seals 26 and 27 on the first valve spool have moved away from the first source port so as to leave it open to flow. Now the first source port and the common port are connected. This is the other active setting of this valve (FIG. 3).

As can be seen from the foregoing, from the rest position, the surgeon moves the second spool to its first active position, connecting the second source to the common port. The next increment closes the second source port and opens the first. The surgeon need merely shift between these two incremental positions to select the desired function. Then when he needs neither, he merely releases the actuator (i.e, the second valve spool) and the valve closes entirely.

This is a rugged device, simple to use. It can be cleaned and sterilized, but its cost is so low as to be a disposable item.

Attention is called to scallops 60,61, and to the flat shape of the body. The surgeon's fingers can conveniently fit in these scallops so that he can grip this valve as a joystick or as a pistol. This provides significant convenience for the surgeon.

Some surgeons may wish for indication of the setting of the valve when the valve is not closed, so as to assure him of the direction of flow other than by observation through the endoscope. This invention enables tactile, visual, and audible means to be provided for this purpose.

In FIG. 1 a transparent window 69 is shown, enabling the surgeon to see what is flowing in common channel 12. This will provide a visible indication of the setting.

Figure 4:
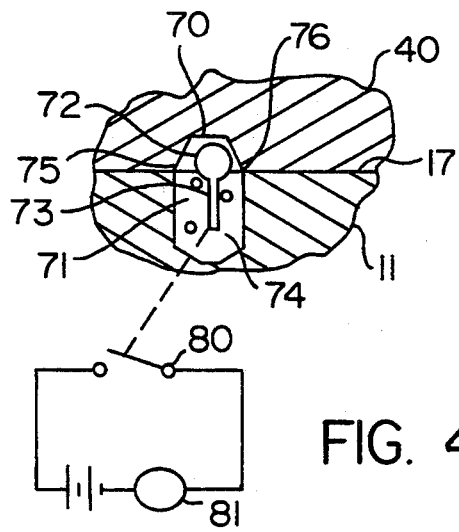
FIG. 4 is a fragmentation view, partly in schematic notation showing an optional feature of the invention.

In FIG. 4, tactile means is shown. It should be remembered that only two mutually exclusive active valve positions are available, and that both valve spools cannot be in the open position at the same time. A peripheral groove 70 is formed in the wall of second valve spool 40. A socket 71 is formed in wall 17 of valve bore 15. A ball 72 with a rigid tail 73 is placed in the socket. A bias spring 74 in the socket biases the ball toward the spool. The groove has slanting shoulders 75,76 so that the ball can be pressed into the socket by the valve spool except when the groove is centered over the ball. The ball and groove are so disposed and arranged that the ball will be in the groove when the second valve spool has been moved to open its port. The surgeon can feel this effect. The detention is weak enough that the bias springs can readily return the spool.

A second ball and groove assembly is formed in the first valve spool 25 identical to that already described, and is therefore not illustrated. When the first valve spool moves to its open position, this detent action will occur. However, because this valve opens at the end of the spool travel, it is not necessary, because the surgeon can feel that the valve is open. Still it can be provided.

The detent does, however, provide for indicative means to indicate the valve setting. The tails on the balls may be linked to respective switching means 80 to which control indicia means 81 such as an audible tone generator to provide a tone respective to each valve setting, or even actuate a light to provide yet another visible means to indicate the valve setting.

This invention is not to be limited by the embodiments shown in the drawings and described in the description, which are given by way of example and not of limitation, but only in accordance with the scope of the appended claims.

I claim:

1. A single axis three way selector valve for connecting a common channel to one or the other of two sources, or to neither source, comprising:

a valve body having said common channel, and a valve bore having a linear axis and a cylindrical wall;

a common port interconnecting said valve bore and said common channel, a first source port and a second source port both passing into the body and opening into said valve bore, one on each axial side of the common port;

a first valve spool on the same axial side of the common port as the first source port, a pair of peripheral sliding seals around said first valve spool axially spaced apart so as to span said first source port in the rest position of said first valve spool, first spring bias means pressing said first valve spool toward said rest position, and stop means on said body and said first valve spool limiting the movement of said first valve spool toward said common port to said rest position, and contact means on said first valve spool;

a second valve spool on the same side of the common port as the second source port, two pairs of peripheral sliding seals around said second valve spool axially spaced apart from one another, a peripheral inlet relief in the surface of said second valve spool between the adjacent seals, one from each pair, said seals being so disposed and arranged that adjacent ones of said seals can span said second source port, a flow passage in said second valve spool interconnecting said peripheral inlet relief and the valve bore, by-passing one of said pairs of seals, a second spring bias means pressing said second valve body toward a rest position farthest removed from said common port where it closes said second source port, and stop means on said body and said second valve spool limiting the movement of said second valve spool away from said common port to said rest position, and contact means on said second valve spool, said contact means being spaced apart sufficiently to permit said second valve spool to more from its rest position to open said second source port, thereafter to engage and upon further axial movement also to move said first valve spool to open said first source port and close said second source port, said common port always being open.

2. A valve according to claim 1 in which said body is scalloped to permit grasping of the body in a pistol type grip or in a joystick type grip.

3. A valve according to claim 1 in which said second valve spool includes a shaft protruding beyond the body.

4. A valve according to claim 1 in which transparent means is formed in the valve body to enable observation of flow through the valve.

5. A valve according to claim 1 in which tactile means to indicate the position of the second valve spool is formed in the wall of the valve bore and in said second valve spool.

6. A valve according to claim 5 in which said tactile means comprises a recess in said second valve spool, and a spring-loaded ball in a socket in the wall of said valve bore, said ball entering said recess when the second valve spool is set to open its respective source port.

7. A valve according to claim 5 in which a second said tactile means is formed between the first valve spool and the wall of the valve bore.

8. A valve according to claim 1 in which switch means responsive to the position of the second valve spool controls indicia means to indicate when the second valve spool has moved to open its respective source port.

9. A valve according to claim 8 in which said indicia means provides a visual or an audible indication of the valve setting.

* * * * *